(12) United States Patent
Guo et al.

(10) Patent No.: US 11,286,309 B2
(45) Date of Patent: Mar. 29, 2022

(54) ANTIHUMAN PCSK9 MONOCLONAL ANTIBODY AND APPLICATION THEREOF

(71) Applicant: ZHEJIANG BLUE SHIELD PHARMACEUTICAL CO., LTD., Shaoxing (CN)

(72) Inventors: Zhigang Guo, Shaoxing (CN); Li Jing, Shaoxing (CN); Ali Wajid, Shaoxing (CN)

(73) Assignee: ZHEJIANG BLUE SHIELD PHARMACEUTICAL CO., LTD., Shaoxing (CN)

( * ) Notice: Subject to any disclaimer, the term of this patent is extended or adjusted under 35 U.S.C. 154(b) by 107 days.

(21) Appl. No.: 16/732,369

(22) Filed: Jan. 2, 2020

(65) Prior Publication Data

US 2020/0223943 A1 Jul. 16, 2020

Related U.S. Application Data

(63) Continuation-in-part of application No. PCT/CN2019/084876, filed on Apr. 29, 2019.

(51) Int. Cl.
*C07K 16/40* (2006.01)
*A61K 39/395* (2006.01)
*A61P 35/00* (2006.01)
*A61K 39/00* (2006.01)

(52) U.S. Cl.
CPC ........ *C07K 16/40* (2013.01); *A61K 39/39583* (2013.01); *A61P 35/00* (2018.01); *A61K 2039/505* (2013.01); *C07K 2317/24* (2013.01); *C07K 2317/55* (2013.01); *C07K 2317/565* (2013.01)

(58) Field of Classification Search
CPC combination set(s) only.
See application file for complete search history.

(56) References Cited

U.S. PATENT DOCUMENTS 9,920,134 B2 * 3/2018 Jackson ............... A61K 39/395

\* cited by examiner

*Primary Examiner* — Laura B Goddard
*Assistant Examiner* — Sarah A Alsomairy
(74) *Attorney, Agent, or Firm* — CBM Patent Consulting, LLC

(57) ABSTRACT

The invention discloses a brand-new PCSK9 antibody. The PCSK9 antibody is sieved through a phage display technology, then a full-length gene sequence is obtained through a gene engineering technology, and applied to preparation of the antibody, and the prepared antibody is high in yield and short in period and is a humanized antibody. The invention further discloses an anti-tumor effect of the antihuman PCSK9 antibody, which expands the way of thinking for research on occurrence and development of tumors in the future, and lays foundations for preparing the antihuman PCSK9 antibody into monoclonal antibody medicines used for treating tumors in the later period.

9 Claims, 3 Drawing Sheets

Specification includes a Sequence Listing.

SEQUENCE LISTING

<160> NUMBER OF SEQ ID NOS: 9

<210> SEQ ID NO 1
<211> LENGTH: 5
<212> TYPE: PRT
<213> ORGANISM: Artificial Sequence
<220> FEATURE:
<223> OTHER INFORMATION: It is synthesized.

<400> SEQUENCE: 1

Gly Tyr Val Leu Asn
1               5

<210> SEQ ID NO 2
<211> LENGTH: 16
<212> TYPE: PRT
<213> ORGANISM: Artificial Sequence
<220> FEATURE:
<223> OTHER INFORMATION: It is synthesized.

<400> SEQUENCE: 2

His Ile Asn Val Cys Arg Glu Ser Phe Tyr Asn Gln Lys Phe Lys Asp
1               5                   10                  15

<210> SEQ ID NO 3
<211> LENGTH: 9
<212> TYPE: PRT
<213> ORGANISM: Artificial Sequence
<220> FEATURE:
<223> OTHER INFORMATION: It is synthesized.

<400> SEQUENCE: 3

Gly Gly Met Val Cys Glu Ser Asp Tyr
1               5

<210> SEQ ID NO 4
<211> LENGTH: 13
<212> TYPE: PRT
<213> ORGANISM: Artificial Sequence
<220> FEATURE:
<223> OTHER INFORMATION: It is synthesized.

-continued

<400> SEQUENCE: 4

Ser Gly Phe Gln Asn Ile Val Gly His Leu Lys Leu Glu
1               5                   10

<210> SEQ ID NO 5
<211> LENGTH: 8
<212> TYPE: PRT
<213> ORGANISM: Artificial Sequence
<220> FEATURE:
<223> OTHER INFORMATION: It is synthesized

<400> SEQUENCE: 5

Lys Val Gly Tyr Leu Val Phe Ser
1               5

<210> SEQ ID NO 6
<211> LENGTH: 9
<212> TYPE: PRT
<213> ORGANISM: Artificial Sequence
<220> FEATURE:
<223> OTHER INFORMATION: It is synthesized.

<400> SEQUENCE: 6

Phe Gln Gly Phe Ser Val Thr Tyr Thr
1               5

<210> SEQ ID NO 7
<211> LENGTH: 438
<212> TYPE: PRT
<213> ORGANISM: Artificial Sequence
<220> FEATURE:
<223> OTHER INFORMATION: It is synthesized

<400> SEQUENCE: 7

Glu Val Gln Leu Glu Glu Ser Gly Pro Glu Leu Val Lys Pro Ser Phe
1               5                   10                  15

Val Val Lys Ile Ser Cys Lys Ala Ser Gly Tyr Ser Phe Thr Gly Tyr
                20                  25                  30

Val Leu Asn Trp Val Arg Gln Ser His Lys Val Leu Trp Ile Gly His
            35                  40                  45

Ile Asn Val Cys Arg Glu Ser Phe Tyr Asn Gln Lys Phe Lys Asp Lys
        50                  55                  60

Ala Ser Leu Thr Ser Arg Thr Ala His Val Tyr Ile Lys Met Leu Thr
65                  70                  75                  80

Ser Glu Asp Ser Ala Val Tyr Tyr Cys Val Arg Gly Gly Met Val Cys
                85                  90                  95

Glu Ser Asp Tyr Trp Gly Gln Gly Thr Ser Val Thr Val Ser Ser Ala
            100                 105                 110

Ser Thr Lys Gly Pro Ser Val Met Pro Leu Ala Pro Cys Ser Arg Ser
        115                 120                 125

Thr Ser Glu Ser Thr Ala Ala Leu Gly Val Leu Val Lys Asp Tyr Phe
130                 135                 140

Thr Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Lys Thr Tyr
            180                 185                 190

Thr Cys Asn Val Asp His Lys Pro Ser Asn Thr Lys Val Asp Lys Arg
            195                 200                 205

Val Glu Ser Lys Tyr Gly Pro Pro Cys Pro Pro Cys Pro Ala Pro Glu
    210                 215                 220

Phe Leu Gly Gly Pro Ser Val Phe Leu Phe Pro Pro Lys Pro Lys Asp
225                 230                 235                 240

Thr Leu Met Ile Ser Arg Thr Pro Glu Val Thr Cys Val Val Val Asp
            245                 250                 255

Val Ser Gln Glu Asp Pro Glu Val Gln Phe Asn Trp Tyr Val Asp Gly
        260                 265                 270

Val Glu Val His Asn Ala Lys Thr Lys Pro Arg Glu Glu Gln Phe Asn
    275                 280                 285

Ser Thr Tyr Arg Val Val Ser Val Leu Thr Val Leu His Gln Asp Trp
        290                 295                 300

Leu Asn Gly Lys Glu Tyr Lys Cys Lys Val Ser Asn Lys Gly Leu Pro
305                 310                 315                 320

Ser Ser Ile Glu Lys Thr Ile Ser Lys Ala Lys Gly Gln Pro Arg Glu
            325                 330                 335

Pro Gln Val Tyr Thr Leu Pro Pro Ser Gln Glu Glu Met Thr Lys Asn
        340                 345                 350

Gln Val Ser Leu Thr Cys Leu Val Lys Gly Phe Tyr Pro Ser Asp Ile
            355                 360                 365

Ala Val Glu Val Glu Ser Asn Gly Gln Pro Glu Asn Asn Tyr Lys Thr
    370                 375                 380

Thr Pro Pro Val Leu Asp Ser Asp Gly Ser Phe Phe Leu Tyr Ser Arg
385                 390                 395                 400

Leu Thr Val Asp Lys Ser Arg Trp Gln Glu Gly Asn Val Phe Ser Cys
            405                 410                 415

Ser Val Met His Glu Ala Leu His Asn His Tyr Thr Gln Lys Ser Leu
        420                 425                 430

Ser Leu Ser Leu Gly Lys
        435

<210> SEQ ID NO 8
<211> LENGTH: 221
<212> TYPE: PRT
<213> ORGANISM: Artificial Sequence
<220> FEATURE:
<223> OTHER INFORMATION: It is synthesized.

<400> SEQUENCE: 8

Asp Ile Leu Met Thr Gln Thr Pro Leu Thr Tyr Ser Leu Gly Asp Ser
1               5                   10                  15

Ile Ser Cys Ser Gly Phe Gln Asn Ile Val Gly His Leu Lys Leu Glu
            20                  25                  30

Trp Phe Leu Gln Lys Pro Gln Phe Gly Val Lys Leu Leu Ile Tyr Lys
        35                  40                  45

Val Gly Tyr Leu Val Phe Ser Gly Val Pro Asp Arg Phe Ser Gly Ser
    50                  55                  60

Gly Gly Thr His Leu Ile Lys Ile Ser Arg Val Glu Ala Glu Asp Leu
65                  70                  75                  80

Gly Val Tyr Tyr Cys Phe Gln Gly Phe Ser Val Thr Tyr Thr Phe Gly
                85                  90                  95

Gly Gly Thr Lys Leu Glu Ile Lys Phe Gly Gly Gly Thr Lys Trp Glu
            100                 105                 110

```
Ile Lys Arg Thr Ser Ala Ala Pro Ser Val Phe Ile Phe Pro Pro Ser
        115                 120                 125
Asp Glu Gln Leu Lys Ser Gly Thr Ala Ser Val Val Cys Leu Leu Asn
        130                 135                 140
Leu Phe Tyr Pro Arg Glu Ala Lys Val Gln Trp Lys Val Asp Asn Ala
145                 150                 155                 160
Leu Gln Ser Gly Asn Ser Val Glu Ser Val Thr Glu Gln Asp Ser Lys
                165                 170                 175
Asp Ser Thr Tyr Ser Leu Ser Ser Thr Leu Thr Leu Ser Lys Ala Asp
                180                 185                 190
Tyr Glu Lys His Arg Val Tyr Ala Cys Glu Val Thr His Gln Gly Leu
        195                 200                 205
Ser Ser Pro Val Thr Lys Ser Phe Asn Arg Gly Glu Cys
        210                 215                 220

<210> SEQ ID NO 9
<211> LENGTH: 12
<212> TYPE: DNA
<213> ORGANISM: Artificial Sequence
<220> FEATURE:
<223> OTHER INFORMATION: It is synthesized.

<400> SEQUENCE: 9
aagcttgcca cc                                                    12
```

ANTIHUMAN PCSK9 MONOCLONAL ANTIBODY AND APPLICATION THEREOF

This application claims priority to Chinese Patent Application Ser. No. CN201910073758.0 filed on 25 Jan. 2019, and International Application No. PCT/CN2019/084876 filed on 29 Apr. 2019.

TECHNICAL FIELD

The present invention relates to a gene engineering antibody technology, and more particularly, to a preparation method of a fully humanized monoclonal antibody and a full-length antibody aiming at PCSK9 and an application thereof in anti-tumor.

BACKGROUND

PCSK9, formerly known as a Neural Apoptosis-Regulated Convertase 1 (NARC-1), is the $9^{th}$ member of a preprotein convertase subtilisin family discovered and reported for the first time by Canadian biochemist Nabil Seidah and the team. Main physiological functions of the PCSK9 are to mediate degradation of a Low Density Lipoprotein Receptor (LDLR) of a hepatocyte, and reduce uptake of LDL-cholesterol (LDL-c) of plasma by the LDLR, leading to increase of a LDL-c level. Targeted inhibition of the PCSK9 is beneficial for reducing the LDL-c level. Therefore, the PCSK9 becomes a hot new target for lipid lowering, and a PCSK9 inhibitor is emerged. At present, there are about 10 pharmaceutical companies producing and developing the PCSK9 inhibitor, comprising Sanofi, Amgen, Novartis, Pfizer, Squibb, etc. About half of the PCSK9 inhibitors are monoclonal antibodies and are in a leading stage of clinical medicine research. At present, most PCSK9 inhibitors are used to treat dyslipidemia, metabolic diseases, hypercholesterolemia, inflammatory diseases, etc., and few people have studied or reported the tumor inhibiting effects.

A tumor has always been one of major threats to human health, and human beings have also been committed to the study of the tumor, hoping to find more effective methods to treat the tumor. However, there are still unmet medical needs for a more effective and less toxic therapy. Overcoming the tumor has always been a problem that scholars are eager to solve, and through in-depth research on the cause and pathogenesis of the tumor, a series of tumor treatment technologies have been developed now, such as surgical resection, radiotherapy and chemotherapy, etc. However, these methods have shortcomings such as a low cure rate, a large side effect of medicine, etc., and the tumor treatment is still a big problem perplexing the medical field. An antigen corresponding to a monoclonal antibody has a high degree of specificity, and a monoclonal antibody specifically bound to a specific molecular target may be prepared. As a research hotspot in the field of biological medicines, a monoclonal antibody medicine has the characteristics of strong targeting, high specificity and low toxic and side effects, and represents the latest development direction in the field of medicine treatment.

A colon cancer, often referred to as a colorectal cancer or an intestinal cancer, is a cancer derived from uncontrolled cell growth in colon, rectum or appendix, and is the second most commonly diagnosed malignancy and the second most common cause of cancer death in the United States. At present, commonly used targeted medicines in the field of the colorectal cancer comprise two types of medicines targeting an epidermal growth factor receptor (EGFR) (referring to the drawing) and a vascular endothelial growth factor (VEGF), which specifically comprise bevacizumab, cetuximab and panizumab.

At present, technologies for preparing the antibody generally comprise a hybridoma technology and a phage screening technology. Disadvantages of the hybridoma technology for sieving the antibody comprise long time, low yield, and low antibody purity, and the antibody produced by the technology is a murine antibody. Current patents on a preparation method of an antihuman PCSK9 monoclonal antibody are mostly to sieve a PCSK9 antibody through a phage sieving method in an early stage or to prepare a new PCSK9 antibody through a gene engineering method, and there are few methods for transfecting a constructed plasmid into a suspension cell and culturing and preparing the antibody through a cell supernatant in a late stage.

SUMMARY

Object of the invention: aiming at the technical problems in the prior art, the present invention provides an antihuman PCSK9 monoclonal antibody, and provides a preparation method and an application of the antihuman PCSK9 monoclonal antibody in preparing medicines.

Technical solution: the present application provides an antihuman PCSK9 monoclonal antibody, wherein a CDR1, a CDR2 and a CDR3 of a VH of the antibody respectively have an amino acid sequence shown in SEQ ID NO:1-3, and a CDR1, a CDR2 and a CDR3 of a VL of the antibody respectively have an amino acid sequence shown in SEQ ID NO:4-6.

Further, the VH of the antihuman PCSK9 monoclonal antibody has an amino acid sequence shown in SEQ ID NO:7, and the VL of the antihuman PCSK9 monoclonal antibody has an amino acid sequence shown in SEQ ID NO:8.

The antihuman PCSK9 monoclonal antibody above is a fully humanized antibody.

The present invention further discloses an application of the antihuman PCSK9 monoclonal antibody in preparing a medicine for treating a disease mediated by human PCSK9.

Further, the present invention further discloses an application of the antihuman PCSK9 monoclonal antibody in preparing a medicine for treating a cancer, especially a colorectal cancer.

According to the present invention, a humanized monoclonal antibody phage display library constructed and saved (a natural humanized Fab phage display library constructed according to the report of Hans J. W. de Haard et al. (Antibody Phage Display, 2002, p87-100)), with a storage capacity more than $1.0 \times 10^{10}$, and a host of *Escherichia coli* TG1 is utilized to screen an Fab antibody against human PCSK9, and a complete full-length antibody is obtained by genetic engineering; and further, the antibody is found to be capable of effectively inhibiting growth of a colorectal cancer in a mouse model through an experiment, and growth of a tumor in a treatment group is found to be obviously inhibited in comparison with that in a control group through the experiment.

The preparation method of the antihuman PCSK9 monoclonal antibody is as follows.

Step 1: Screening a Target Antibody According to the Phage Library

A certain concentration of PCSK9 antigen is added into an immune tube and coated overnight, and a phage is washed and sealed, and added into the immune tube the next day to bind the antigen and the antibody; the immune tube is repeatedly turned over and stood, then washed with tween 20, and eluted; the eluted phage is neutralized with 1M tris-Hcl and infected with TG1, then a titer is determined and amplification and concentration are performed for next round of screening; after 4 rounds of screening, the eluted phage is infected with Escherichia coli TG1 and subjected to plate coating and monoclonal selection, and ELISA detection is further performed to screen out positive clones; DNA sequencing is performed on the screened antibody (named PA6) to obtain variable region of heavy chain and variable region of light chain sequences of the PA6.

Step 2: Expression and Purification of an Fab Fragment of a Positive Monoclonal PA6 Antibody One of the monoclonal antibodies is selected for TG1 infection, and a plasmid is extracted; after Gene III is removed by enzyme digestion, the plasmid is transformed and subjected to extended culture, and then a colony is collected for purification.

Step 3: Expression and Purification of a Positive Clone in a Full-Length Antibody IgG1 Form 1. Construction of a heavy chain expression plasmid: a CH1-VH part in the Fab fragment of the PA6 antibody is amplified by PCR, and the CH1-VH part is bound to an Fc fragment. A Kozak sequence, a signal peptide and a restriction enzyme site are then added to an N-terminal of a variable region of heavy chain VH. An amplified heavy chain fragment and an expression vector are digested by restriction enzymes NgoMIV and Nhel, and the fragment is bound to the vector after enzyme digestion.

2. Construction of a light chain expression plasmid: a complete light chain part of the Fab fragment of the PA6 antibody is amplified by PCR. A Kozak sequence, a signal peptide and a restriction enzyme site are added to an N-terminal of a variable region of light chain VL. An amplified light chain fragment and an expression vector are digested by restriction enzymes NgoMIV and Nhel, and the fragment is bound to the vector after enzyme digestion.

3. Induced expression: the constructed plasmid is transfected with CHO-S cells by using a transfection reagent, after transfection, when a cell viability recovers to about 90%, the cells are screened with puromycin and added with MTX at the same time for pressurization, with a pressurization concentration gradually increasing from 50 nM to 500 nM until the cells are in a relatively stable state. A supernatant of the cells is taken and ran in gel to identify an expression quantity of the PA6 antibody (FIG. 3); when the antibody is confirmed to be really expressed, the cells are spread into a 96-well plate for positive clone screening and subjected to ELISA detection. The screened positive clone is subjected to extended culture to a 250 ml shake flask and continuously cultured, and regularly added with a supplement. Then a cell supernatant is collected, and corresponding antibodies are purified, and a concentration of the antiboodies is determined (FIG. 4).

Step 4: purification of the cell supernatant: the supernatant at −80° C. above is placed at 4° C. for natural thawing, and the entire supernatant with a volume of about 150 ml is ultrafiltrated and concentrated to a total volume of about 10 ml by using an ultrafiltration tube of 15 ml 50 KD (molecular weight cut-off), diluted twice with a bound buffer, and finally filtered with a 0.45 μm filter membrane. rProtein G Beads are loaded into a 1 ml chromatography column, the chromatography is balanced with a bound solution of 5 times the column volume, then a sample is added into the balanced rProtein G Beads, and then washed with an impurity washing solution of 10 times the column volume, and finally, the bound antibody is eluted with an eluent of 5 times the column volume. The collected eluent is desalted and concentrated by using an ultrafiltration tube of 15 ml 50 KD (molecular weight cut-off), and washed twice with a PBS during the period, and finally, about 1 ml of the concentrated solution is collected, and temporarily stored at 4° C. A concentration of a purified antibody is detected by a Bradford Protein Assay Kit, and the concentration is finally determined to be 2.775 mg/ml. An outflow component, an impurity washing component and an elution component are detected by using SDS-PAGE to observe a purification effect, and finally, a purity is indicated to be more than 95%.

Beneficial effects: on one hand, the present invention utilizes a phage display technology to screen out the brand-new PCSK9 antibody, then obtains the full-length gene sequence through a genetic engineering technology, and applies the full-length gene sequence to antibody preparation, and the prepared antibody has a high yield and a short period, and is a humanized antibody; and on the other hand, an anti-tumor effect of the antihuman PCSK9 antibody is innovatively found (taking the colorectal cancer as an example), which expands the way of thinking for research on occurrence and development of tumors in the future, and lays foundations for preparing the antihuman PCSK9 antibody into monoclonal antibody medicines used for treating tumors in the later period.

DETAILED DESCRIPTION

Figure 1:
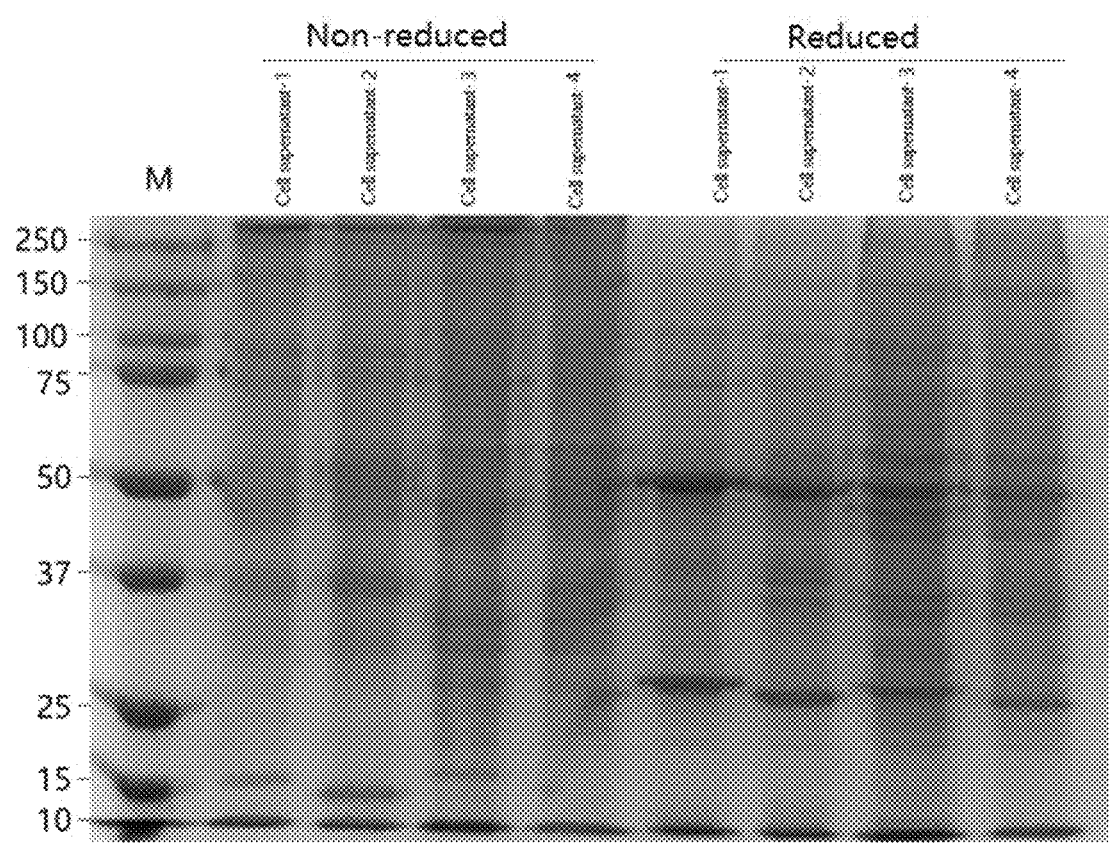
FIG. 1 shows SDS-PAGE identification results of a cell supernatant.

The application is described in detail hereinafter with reference to specific embodiments.

Embodiment 1

Screening of an Fab Phage Library to Obtain an Antihuman PCSK9 Positive Monoclonal Antibody 1. A PCSK9 protein (GenScript Biotech Corporation) was diluted to a concentration of 100 ug/ml, and 1.5 ml of the PCSK9 protein was added into an immune tube, and coated overnight at 4° C. A coating buffer in the immune tube was discarded next day, and washed with a PBS for three times. 2% skimmed milk powder was prepared and sealed in the immune tube for 3 hours to 4 hours. Meanwhile, a natural humanized Fab phage display library constructed according to the report of Hans J. W. de Haard et al. (Antibody PhageDisplay, 2002, p87-100) was also sealed for 1 hour, then a phage was added into the immune tube, and turned over repeatedly for 2 hours, and the phage bound to the immune tube was eluted with 0.1% Tween 20 and neutralized. The neutralized phage was infected with TG1 for next round of screening.

2. After 3 to 5 rounds of screening, the eluted phage was infected with Escherichia coli TG1 (Beyotime, D0389) and subjected to plate coating, then 100 clones were randomly selected for Elisa identification of the phage.

3. The clones were inoculated in a 96-well plate and cultured at 37° C. until $OD_{600}$ reached about 0.5; a VSCM13 auxiliary phage was added, and cultured overnight; and the amplified phages were blocked with the 2% skimmed milk powder, respectively added into an ELISA plate coated with 1 µg/ml PCSK9 antigen and BSA (BSA is negative control), incubated at a room temperature for 1 hour, washed with PBST for 5 times, then added with a rabbit anti-M13 phage HRP conjugate (GE Healthcare Life Sciences), incubated at a room temperature for 1 hour, washed with PBST for 5 times, added with a TMB peroxy substrate, and read at 450 nm wavelength. Finally, a monoclonal antibody No. 6 with a high affinity was screened out as PA6.

4. DNA sequencing was performed on the PA6 to obtain sequences of a variable region of heavy chain (VH) and a variable region of light chain (VL) of the PA6, wherein the complete sequences of the VH and the VL were shown in SEQ ID NO:7 and SEQ ID NO:8, wherein a CDR1, a CDR2 and a CDR3 of the VH respectively had an amino acid sequence shown in SEQ ID NO:1-3, and a CDR1, a CDR2 and a CDR3 of the VL respectively had an amino acid sequence shown in SEQ ID NO:4-6.

Embodiment 2

Expression and Purification of an Fab Fragment of a Positive Monoclonal PA6 Antibody 1. A screened PA6 antibody with a high affinity was infected with TG1 and amplified, then a bacterial liquid was collected, a plasmid was extracted by a plasmid extraction kit (omega, D6950-01), and Gene III of the plasmid was removed.

2. The obtained GeneIII-excised plasmid was transfected into Escherichia coli TG I, cultured in a 2YTA medium at 37° C. to a logarithmic phase, added with 1 mM IPTG, and subjected to induced expression at 37° C. overnight. 3. A supernatant was collected by centrifugation and purified with a Protein A (CWBIO, CW0894S) to obtain a PA6 Fab protein.

Embodiment 3

Expression and Purification of a Positive Clone in a Full-Length Antibody IgG1 Form 1. Construction of a heavy chain expression plasmid: a CH1-VH part in an Fab fragment of a PA6 antibody was amplified by PCR, and the CH1-VH part was bound to a Fc fragment (referring to a variable region gene of a fully humanized monoclonal antibody against PCSK9 and an application thereof for details, with the patent No. CN 104861071 A) stored in a laboratory by using a T4 ligase. Then, a Kozak sequence (SEQ ID NO: 9: AAG CTT GCCACC), a signal peptide and a restriction enzyme site were added to an N-terminal of a variable region of heavy chain VH. An amplified heavy chain fragment and an expression vector UCOE-Mu-P were digested by restriction enzymes NgoMIV and NheI, and the fragment was bound to the vector after enzyme digestion.

2. Construction of a light chain expression plasmid: a complete light chain part of the Fab fragment of the PA6 antibody was amplified by PCR. A Kozak sequence (SEQ ID NO: 9: AAG CTT GCCACC), a signal peptide and a restriction enzyme site were added to an N-terminal of a variable region of light chain VL. An amplified light chain fragment and an expression vector UCOE-Mu-P were digested by restriction enzymes NgoMIV and NheI, and the fragment was bound to the vector after enzyme digestion.

3. Induced expression: the heavy and light chain plasmids expressing the PCSK9 antibody were co-transfected into CHO-S cells (BeNa Bio, 338010) with a transfection reagent; after a cell viability was stable, MTX (50 nm, 100 nm, 200 nm and 500nm) and puromycin (Solarbio, P8230) were added for pressure screening until a cell state was stable, and a cell supernatant was taken and ran in gel to see whether a target antibody thereof was expressed. After the expression was confirmed, the cells were spread into a 96-well plate with an average of 2 cells per well. After the cells grew to a monoclonal state, a supernatant was taken for ELISA detection, after 2 to 3 rounds of subclone screening, then the cells were subjected to extended culture to a 250 ml shake flask, and regularly added with a supplement to increase an antibody production, and the cells in the shake flask were sampled, counted and analyzed when the supplement was added each time. Specifically, as shown in Table 1-3, cell strains stably expressing the antihuman PCSK9 monoclonal antibody were subjected to extended culture, and used to prepare the antibody through shake flask culture, three independent experiments were respectively performed, the cells were extended to the shake flask, and two shake flasks were selected for parallel experiments. Specific results of sample counting of one and/or two shake flasks were randomly taken every 2 days to 3 days and the cells were treated.

TABLE 1

| Time | Cell density ($10^6$) | Cell viability (%) | Cell treatment | Cell culture method |
|---|---|---|---|---|
| May 21, 2018 | 0.8 | 99 | Extended to 250 ml shake flask for 60 ml respectively | CD-FortiCHO + 4 mM of Glutamax + 1% of ACA |
| May 23, 2018 | 2.18/6.20 | 98/98 | Supplemented with 5% of Feed C (with white precipitate on flask body) | |
| May 25, 2018 | 11.6/5.3 | 97/98 | Supplemented with 10% of Feed C | |
| May 28, 2018 | Basically died/2.7 | 10/48.2 | Collected 80 ml of supernatant respectively | |

TABLE 2

| Time | Cell density ($10^6$) | Cell viability (%) | Cell treatment | Cell culture method |
|---|---|---|---|---|
| Jun. 1, 2018 | 0.8 | 99 | Extended to two 250 ml shake flasks for 80 ml respectively | CD-FortiCHO + 4 mM of Glutamax + 1% of ACA |
| Jun. 4, 2018 | 11.3/6.8 | 98/97 | Supplemented with 10% of Feed C | |
| Jun. 6, 2018 | 14.15/8.0 | 98/98 | Supplemented with 10% of Feed C | |
| Jun. 8, 2018 | 4.15/5.8 | 85.3/72.5 | Collected 160 ml of supernatant respectively | |

TABLE 3

| Time | Cell density ($10^6$) | Cell viability (%) | Cell treatment | Cell culture method |
|---|---|---|---|---|
| Jun. 10, 2018 | 0.8 | 95 | Extended to 250 ml shake flask for 60 ml respectively | CD-FortiCHO + 4 mM of Glutamax + 1% of ACA + 1% of HT |
| Jun. 11, 2018 | 1.0 | 98 | Untreated | |
| Jun. 14, 2018 | 4.34 | 98 | Supplemented with 1 ml of Glutamax Supplemented with 10% of Feed2 | |
| Jun. 16, 2018 | 7.56 | 99 | Supplemented with 10% of Feed2 | |
| Jun. 18, 2018 | 10.75 | 99 | Supplemented with 10% of Feed2 | |
| Jun. 21, 2018 | 6.5/5.15 | 97 | Untreated | |
| Jun. 23, 2018 | — | — | Collected 80 ml of supernatant respectively | |

When the cell viability in the shake flask reached 70% or below, the cell supernatant was collected, and a sample was taken for SDS-PAGE identification. Results were shown in FIG. 1. It could be seen that there was really a target band in the supernatant to express the antihuman PCSK9 antibody, and the supernatant was purified in a later stage.

Embodiment 4

Purification of a PCSK9 Monoclonal Antibody

1. Preparation of a Buffer

Water and a buffer were filtered with a 0.45 μm filter membrane before use.

Binding/impurity washing buffer: 0.15 M NaCl, 20 mM Na2HPO4, pH 7.0.

Elution buffer: 0.1 M glycine, pH 3.0.

Neutralization buffer: 1 M Tris-HCl, pH 8.5.

2. Preparation of a Sample

The supernatant at −80° C. above was placed at 4° C. for natural thawing, and the entire supernatant with a volume of about 150 ml was ultrafiltrated and concentrated to a total volume of about 10 ml by using an ultrafiltration tube (Thermo) of 15 ml 50 KD (molecular weight cut-off), diluted twice with the bound buffer, and finally filtered with the 0.45 μm filter membrane to reduce impurities, thus improving a protein purification efficiency and preventing a column from blockage.

3. Purification of the Sample 1) rProtein G Beads were loaded into a 1 ml chromatography column, and chromatography was balanced with a bound solution of 5 times the column volume, so that a filler was placed in the same buffer system as the target antibody to protect the antibody.

2) The sample was added into the well-balanced rProtein G Beads to ensure full contact between the target antibody and the rProtein G Beads, thus improving a recovery rate of the target antibody, and an outflow was collected.

3) The sample was washed with an impurity washing solution of 10 times the column volume to remove a non-specifically adsorbed foreign protein, and the impurity washing solution was collected.

4) The bound antibody was eluted with an eluent of 5 times the column volume, and the eluent was collected into a centrifuge tube added with the neutralized buffer in advance (5 ml of eluent was added with 0.5 ml of neutralized buffer), namely a target antibody component.

5) The collected eluate was desalted and concentrated by using an ultrafiltration tube of 15 ml 50 KD (molecular weight cut-off), and washed twice with a PBS during the period, and finally, about 1 ml of the concentrated solution was collected, and temporarily stored at 4° C. for concentration and purity detection.

4. Concentration and Purity Detection of a Purified Antibody

Figure 2:
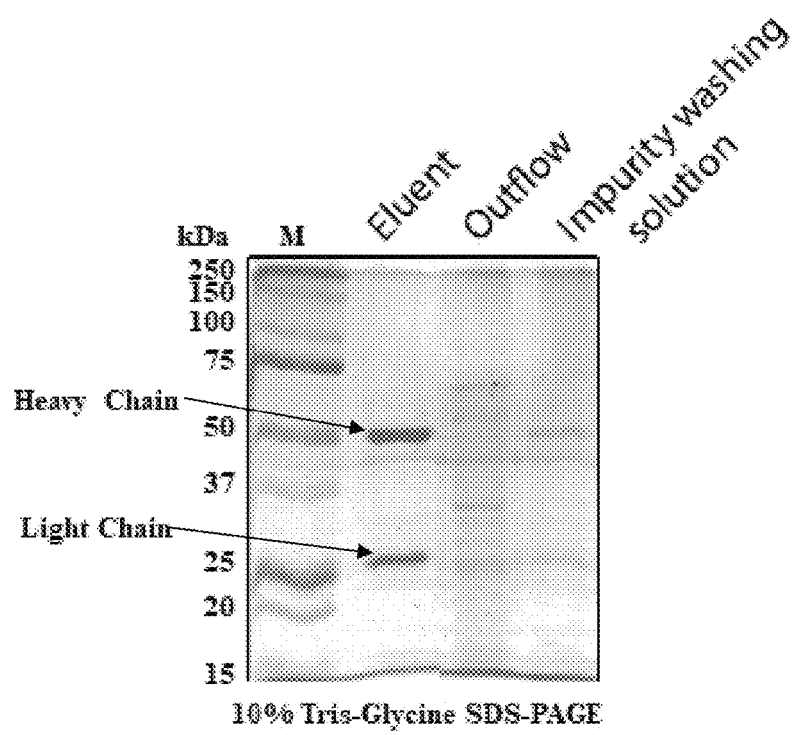
FIG. 2 shows SDS-PAGE detection results of a PCSK9-purified antibody.

A concentration of a purified antibody was detected by a Bradford Protein Assay Kit, and the concentration was finally determined to be 2.775 mg/ml. An outflow component, an impurity washing component and an elution component were detected by using SDS-PAGE to observe a purification effect, and as shown in FIG. 2, according to the arrow in the figure, obvious heavy and light chain belts appeared after sample reduction, and finally, the purity was indicated to be more than 95%.

Embodiment 5

Application of an Antihuman PCSK9 Antibody Obtained Above in Treating a Tumor After the antibody is purified, a concentration was marked, and the antibody was sub-packaged and stored at −80° C. A colon cancer cell (BeNa Bio, BNCC100275) was inoculated to a mouse, the PCSK9 antibody was used to treat the mouse, and a tumor size was observed. Specific operation steps were as follows:

1. 10 female nude mice in 6 weeks were purchased, SW480 cells were extended into 12 large dishes of 10 cm, and a cell inoculation amount of each mouse was ensured to be $5\times10^6$.

2. The cells were digested by trypsin, and collected, and a cell inoculation amount of each mouse was ensured to be $5\times10^6$. The 10 nude mice were divided into a control group and an antibody group, the cells were injected subcutaneously, and the mice were observed until a tumor grew to a certain size (about 200 $mm^3$ in volume).

3. The PCSK9 antibody was prepared, and each nude mouse in the antibody group was injected with a dose of 10 mg/g in a tail intravenous mode according to a body weight; and the nude mice in the control group were injected with the same volume of normal saline, a tumor size of each nude mouse was measured every other week, and the antibody was continuously injected. Then, the tumor size was measured, and the experiment operation was repeated every week for one month.

Figure 3:
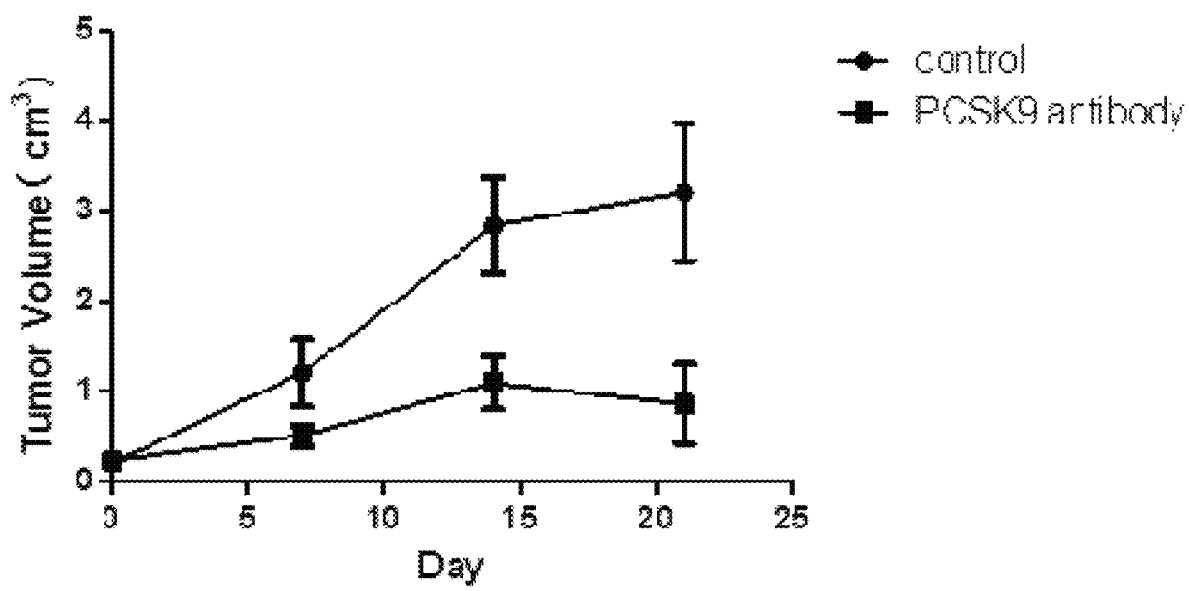
FIG. 3 is a tumor inhibition curve of an antibody to nude mice.
Figure 4:
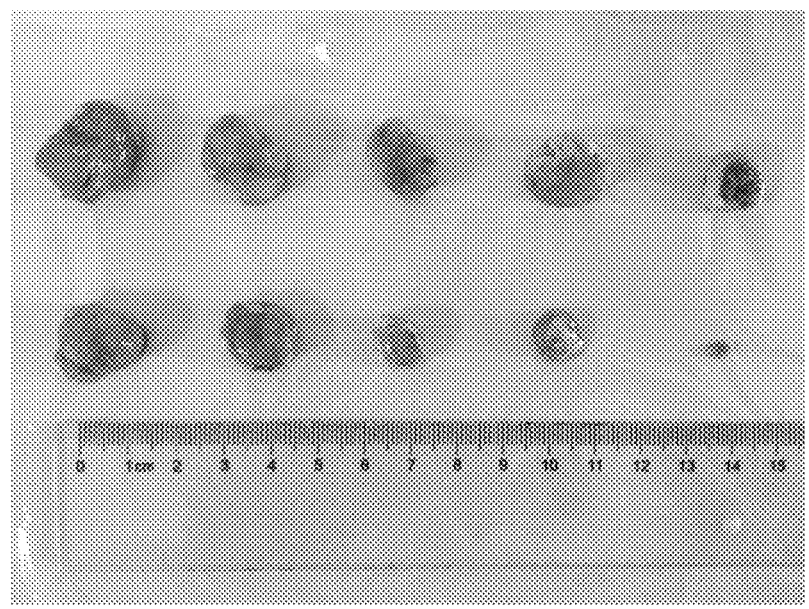
FIG. 4 shows inhibition of the antibody on a tumor size of the nude mice.

4. Finally, tumors of the nude mice were taken out, and tumor sizes of the experimental group and the control group were compared and analyzed. Results were shown in FIG. 3 and FIG. 4. As shown in FIG. 3, after the tumor sizes of the nude mice were analyzed, tumor growth of the treatment group was found to be obviously inhibited compared with that of the control group. As shown in FIG. 4, the tumors of the mice were taken out, and the upper row was the control group and the lower row was the treatment group. The results showed that the tumor growth of the antibody group was significantly inhibited compared with that of the control group.

---

What is claimed is:

1. An antihuman PCSK9 monoclonal antibody comprising a heavy chain and a light chain, wherein the heavy chain having an amino acid sequence shown in SEQ ID NO: 7 and the light chain having an amino acid sequence shown in SEQ ID NO: 8.

2. The antihuman PCSK9 monoclonal antibody according to claim 1, wherein the antihuman PCSK9 monoclonal antibody is a fully humanized antibody.

3. The antihuman PCSK9 monoclonal antibody according to claim 1, wherein the antihuman PCSK9 monoclonal antibody contains an Fab fragment.

4. The antihuman PCSK9 monoclonal antibody according to claim 1, wherein the heavy chain contains a CDR1, a CDR2 and a CDR3 having an amino acid sequence shown in SEQ ID NO: 1, SEQ ID NO: 2 and SEQ ID NO: 3, respectively.

5. The antihuman PCSK9 monoclonal antibody according to claim 1, wherein the light chain contains a CDR1, a CDR2 and a CDR3 having an amino acid sequence shown in SEQ ID NO: 4, SEQ ID NO: 5 and SEQ ID NO: 6, respectively.

6. A pharmaceutical composition for treating a cancer comprising an effective amount of the antihuman PCSK9 monoclonal antibody of claim 1.

7. The pharmaceutical composition for treating the cancer according to claim 6, wherein the cancer is a colorectal cancer.

8. A method for treating a cancer comprising a step of administering to a subject in need of treatment by the antihuman PCSK9 monoclonal antibody of claim 1.

9. The method according to claim 8, wherein the cancer is a colorectal cancer.

* * * * *